United States Patent [19]

Lee

[11] Patent Number: 4,901,708
[45] Date of Patent: Feb. 20, 1990

[54] VIEWING LARYNGOSCOPE

[76] Inventor: Tzium-Shou Lee, 924 Maple Rd., Flossmoor, Ill. 60422

[21] Appl. No.: 222,939

[22] Filed: Jul. 22, 1988

[51] Int. Cl.$^4$ .............................................. A61B 1/06
[52] U.S. Cl. ...................................... 128/11; 128/18; 128/16; 128/6
[58] Field of Search ...................... 128/10, 11, 6, 3, 15, 128/16, 18

[56] References Cited

U.S. PATENT DOCUMENTS

| | | | |
|---|---|---|---|
| 2,354,471 | 7/1944 | MacIntosh | 128/10 |
| 3,091,235 | 5/1963 | Richards | 128/6 |
| 3,638,644 | 2/1972 | Reick | 128/16 |
| 4,086,919 | 5/1978 | Ballard | 128/11 |
| 4,306,547 | 12/1981 | Lowell | 128/11 |
| 4,583,527 | 4/1986 | Maslcant et al. | 128/11 |
| 4,592,393 | 6/1986 | Upshur | 128/11 |

Primary Examiner—Edward M. Coven
Assistant Examiner—M. Graham
Attorney, Agent, or Firm—Hill, Van Santen, Steadman & Simpson

[57] ABSTRACT

A laryngoscope curved blade includes a pair of fiber optic bundles, one fiber optic bundle adapted to transmit light to the distal end of the blade and the other fiber optic bundle adapted to provide a viewing channel for telescopic viewing of the area adjacent to the distal end of the blade. A lens attached to the proximal end of the blade gathers and focuses the light transmitted by the viewing channel fiber optic bundle. Additionally, a lamp located on the proximal end of the blade provides illumination down the throat of a patient for line of sight viewing of the person performing the largyngoscope and the light transmitted by the first fiber optic bundle for illumination of the area adjacent to the distal end of the blade.

7 Claims, 1 Drawing Sheet

U.S. Patent　　　　Feb. 20, 1990　　　　4,901,708
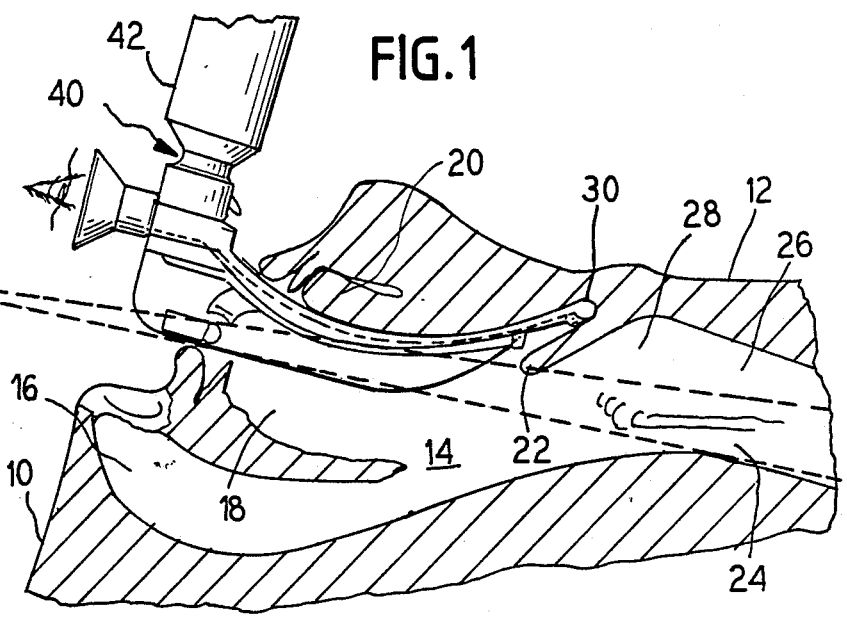
FIG.1
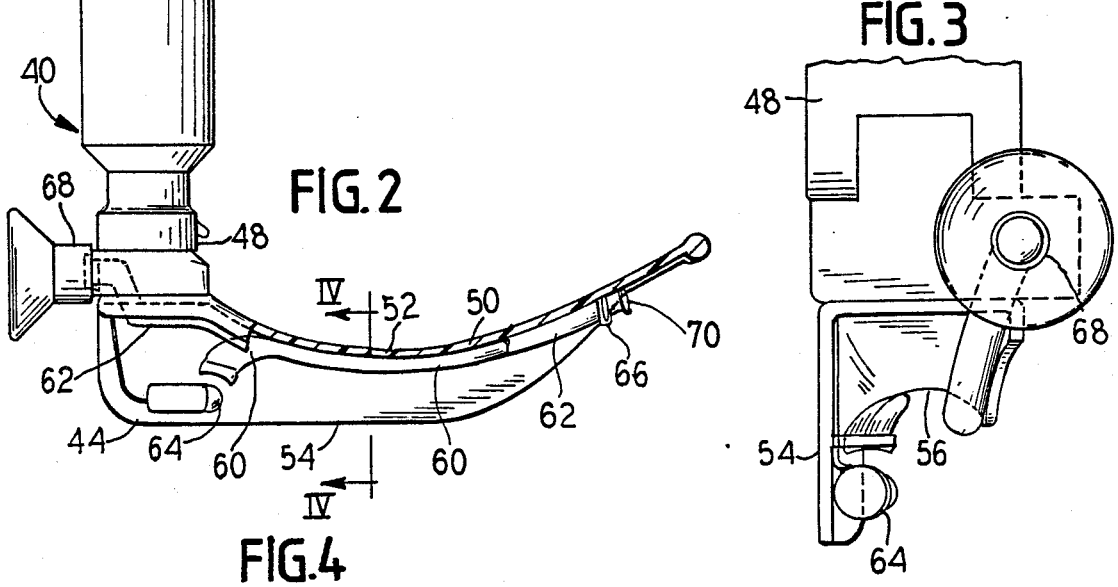
FIG.2
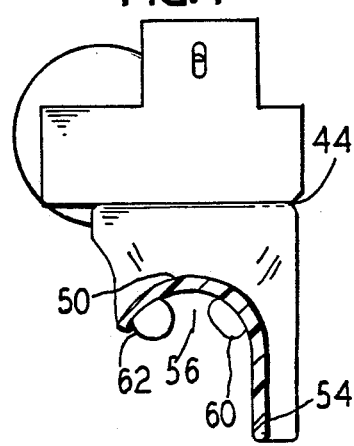
FIG.3
FIG.4
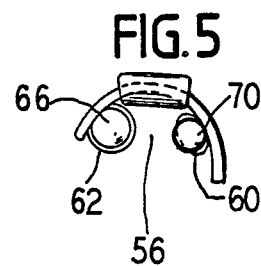
FIG.5

VIEWING LARYNGOSCOPE

BACKGROUND OF THE INVENTION

The present invention relates generally to medical diagnostic and surgical instruments and, in particular, to an improved laryngoscope including a blade incorporating fiber optic bundles thereon.

A human, like most vertebrates, has a plurality of internal passageways, tracts, tubes or pipes communicating between the mouth and the stomach or the lungs. The pharynx is a tract that extends from the nasal cavities to the larynx. The larynx is the upper part of the respiratory tract between the pharynx and the trachea, having cartilaginous walls and containing vocal cords enveloped in folds of mucous membranes attached to the sides. The trachea is a thin-walled tube of cartilaginous and membraneous tissue communicating between the larynx and the lungs to carry air to and from the lungs. The esophagus is a digestive tract communicating between the pharnyx in the area of the larynx and the stomach to carry food to the stomach.

The esophagus and trachea are positioned side-by-side and terminate in the area of the larynx. Thus, both food and air use the common pharynx between the mouth and the nasal cavities and the larynx area.

To prevent food from entering the larynx, a valve member called the epiglottis is provided on the outlet side of the larynx, just above the vocal cords. The epiglottis is a piece of leaf-like tissue composed of cartilage covered by mucous membrane and functions as a lid to cover the entrance to the larynx or voice organ during the act of swallowing. The mucous membrane of the epiglottis is loose and extends to the root (beginning) of the tongue. In doing so, it forms several folds. One that extends to the mid-line of the tongue is called median glosso epiglottic fold. A fold that goes to the side of the tongue is called the lateral glosso epiglottic fold. Between the median fold just described and the lateral fold, there is a natural depression or groove. This natural depression or groove is called the vallecula epiglottica, vallecula being a generic term for a shallow depression or groove. There is one such vallecula on each side of the median glosso epiglottic fold, i.e., a left and right vallecula.

A laryngoscope is a device that enables one to view into the larynx of a patient. Moreover, the laryngoscope assists in the intubulation or insertion of endoscopes down the trachea or esophagus of a patient by stretching the pharynx or throat sufficiently to permit passage of the endoscope while allowing viewing of the endoscope as it is inserted. Endoscopes are tubular instruments combining a light system and a telescopic system used in the visualization of the interior of a member such as an organ, and are adaptable for diagnostic, therapeutic and surgical procedures.

Laryngoscopes are formed of two main members: a handle member and a blade member. The handle member generally is a cylinder adapted to receive therein, batteries for powering a light source such as a lamp. The handle member includes an attaching or lock portion to which the blade member is operatively attached.

The blade member is generally one of two types: straight or curved. The curved type of a blade member is better suited for persons of normal anatomical configuration while the straight type blade member is better suited for persons with certain abnormally configured larynxes.

Either type of blade member includes a spatula portion and, generally, an upstanding leg portion. Each blade member is elongated and extends from a proximal end attached to the handle member to a distal end which is inserted into the patient's throat.

Laryngoscopy is the visual examination of the exterior and interior of the larynx by means of the laryngoscope. During a laryngoscopy, the blade of the laryngoscope is inserted into the throat or pharynx of the patient and the tip of the distal end of the blade is placed into the vallecula epiglottica, i.e., the depression formed at the base of the tongue and the epiglottis. With slight pressure, the blade causes the epiglottis to lift up, thereby exposing the larynx to the view of the medical professional performing the laryngoscopy.

Several features have been incorporated in the blade members to improve the viewing by the medical professional. On some blade members, the spatula includes a concave portion at the mid-portion to provide a tunnel along the length of the blade member through which the line of sight of the medical professional extends. Furthermore, lamps have been incorporated on some blade members to provide illumination into the interior of the patient's pharynx.

In some instances, the anatomical variations of the human throat are such that even when using a standard curved blade, the vocal cords can lie out of the direct vision line of the medical professional inserting the laryngoscope blade member. Thus, the medical professional will not have a clear view of the vocal cords when inserting the blade of a laryngoscope. This can be critical because the blade can be inserted such that the patient's throat is subject to trauma. Thus, it is highly desirable to provide a medical professional with the ability to view the area adjacent the distal end of a curved laryngoscope blade member so that trauma to the throat of a patient can be avoided.

SUMMARY OF THE INVENTION

In accordance with principles of the present invention, a laryngoscope is provided that enables a medical professional performing a laryngoscopy to have a clear view of the area adjacent the distal tip of a curved type laryngoscope blade member while inserting the blade member into the throat of a patient. To this end, fiber optic bundles are incorporated along a blade member, one fiber optic bundle transmitting light from a light source located near the proximal end of the blade member to a point along the distal end of the blade member and another fiber optic bundle being coupled to a lens located at the proximal end of the blade member to provide telescopic viewing of the area adjacent the distal end of the blade member.

By utilizing fiber optic bundles, it is possible to cause the transmission of light to occur around the bend of a curved blade. In this manner, irrespective of the physical location of the vocal cords or other anatomical features under examination, the area in proximity to the tip of the blade member is fully viewable.

Further, by appropriate placement of the fiber optic bundles, there is no interference with the normal view area along the spatula portion of the blade member. Additionally, the light source transmitting fiber optic bundle has a wide dispersion optic at its distal end so as to illuminate not only the area proximate to the distal end of the blade member, but to illuminate the throat of a patient along the normal line of sight of the user performing the laryngoscopy.

In one embodiment, the fiber optic bundles are placed at the sides of the blade member so as not to interfere with the normal tube passage channel formed by the concave tunnel down the center of the spatula portion of the blade member. In another embodiment, the fiber optic bundles are placed outside of the normal side reach of the blade member.

It is an object to provide an improved curved blade laryngoscope. It is another object to provide telescopic viewing of the area adjacent the distal end of a blade member of a curved blade laryngoscope.

It is a further object to provide illumination of the area adjacent the distal end of a blade member of a curved blade laryngoscope.

It is yet a further object to provide illumination of the area adjacent the distal end of a blade member of a curved blade laryngoscope that is dispersed widely.

BRIEF DESCRIPTION OF THE DRAWINGS

FIG. 1 is a side elevational view of a laryngoscope embodying principles of the invention illustrating the performance of a laryngoscopy on a patient;

FIG. 2 is a side elevational view, partially broken away, of the laryngoscope of FIG. 1;

FIG. 3 is a partial proximal end view of the laryngoscope of FIG. 1 illustrating the proximal end of the blade member;

FIG. 4 is a cross-sectional view of the laryngoscope of FIG. 1 taken along the line IV—IV of FIG. 2; and FIG. 5 is a fragmentary distal end view of the laryngoscope of FIG. 1 illustrating the distal ends of the fiber optic bundles.

DETAILED DESCRIPTION OF THE PRESENTLY PREFERRED EMBODIMENT

The present invention provides a laryngoscope which allows for viewing around the bend of a curve blade member thus enabling viewing of the area adjacent the distal end of the blade member. To this end, fiber optic bundles are incorporated along a laryngoscope blade member, one bundle providing light transmission from a light source located near the proximal end near the blade member to the distal end of the blade member and another bundle coupled to a lens located at the proximal end of the blade member to provide telescopic viewing of the area adjacent the distal end of the blade member.

In FIG. 1 there is illustrated a cross-sectional view of a head 10 and a neck portion 12 of a human or patient positioned lying on his or her back. The patient is illustrated as being subjected to a laryngoscopy.

In the cross-sectional view, the patient's pharynx 14 (formed of nasal cavities 16 and mouth 18), tongue 20, epiglottis 22, esophagus 24, trachea 26, and larynx 28 are shown. Additionally shown is the patient's vallecula epiglottica 30, formed at the base of the tongue 20 and the epiglottis 22.

A laryngoscope 40, embodying principles of the invention and more fully illustrated in FIG. 2, is utilized in the laryngoscopy illustrated in FIG. 1. The laryngoscope 40 includes two basic members: a handle member 42 and a curved blade member 44.

As illustrated most fully in FIGS. 2 and 3, the handle member 42 includes an attaching or locking portion 48 to which the blade member 44 is operatively attached. Such handle members are readily available from a variety of manufacturers in the art.

The handle member 42 is cylindrically shaped and is adapted to receive batteries therein that provide a portable power source for the laryngoscope. The batteries are inserted into the handle member 42 by removal of a cover 48 located on one end of the handle member 42.

The blade member 44 includes a spatula portion 50 formed as an elongated member curved about a midpoint 52. The blade member 44 further includes an upstanding leg 54 which runs perpendicularly along one edge of the spatula member 50. The right angle formed by the upstanding leg 54 and the spatula member 50 is more clearly illustrated in FIGS. 3 and 4.

In FIGS. 3 and 4, it is illustrated that the spatula member 50 includes a concave channel 56 running along its length. The channel 56 is provided to allow a medical professional to have a greater line of sight view along the blade member 44 when performing a laryngoscopy and to provide a channel that accommodates a tubular portion of an endoscope, not illustrated.

As illustrated in FIGS. 2-5, the blade member 44 includes a pair of fiber optic bundles 60 and 62 affixed thereon. The fiber optic bundle 60 is adapted to transmit light produced by a lamp 64, operatively coupled to the batteries in the handle member 42, to the distal end of the blade member 44. The fiber optic bundle 62 is adapted to provide a telescopic viewing channel from the distal end to the proximal end of the blade member 44.

A lens member 66 and a lens member 68, located at opposite ends of the fiber optic bundle 62, cooperate to provide telescopic viewing. The lens 66 is located on the distal end of the fiber optic bundle 62 and serves to gather the light at that end and to focus it at the distal end of the bundle 62. A lens member 68 located at the proximal end of the blade member 44 gathers the light transmitted from the distal end of the blade member and expands it to provide an enlarged image at the proximal end of the blade member 44 for the person performing the laryngoscopy. Thus, the person performing the laryngoscopy enjoys a telescopic view of the area adjacent the distal end of the blade member 44.

As illustrated most clearly in FIGS. 4 and 5, the fiber optic bundles are positioned along the concave channel 56 of the spatula member 50. The fiber optic bundles 60 and 62 are small enough and spaced sufficiently far from each other so as not to block viewing along the spatula member 50 along the concave channel 56 or to block the space in the channel 56 through which the tubular member of an endoscope can be inserted.

Furthermore, as illustrated in FIG. 5, the fiber optic bundle 60 includes a lens 70 located on the distal end thereof to provide a wide dispersion of light to illuminate the throat of the patient, as well as the area in proximity to the distal end of the blade member 44.

As illustrated in FIG. 2, in the presently preferred embodiment, the fiber optic bundle 60 does not extend the full length of the blade member 44. The reason for this is that it is preferable to provide light at a point of the blade member 44 at which the light will not be fully covered by throat tissue upon insertion of the blade member 44 into the throat of the patient.

In use during the performance of a laryngoscopy, as illustrated in FIG. 1, the blade member 44 of the laryngoscope 40 is inserted into the mouth 18 of the patient. The blade member 44 supports the tongue 20 and opens the pharynx 14 to provide a line of sight down the throat of the patient for the person performing the laryngoscopy. As illustrated, the tip of the blade member 44 is inserted into the vallecula epiglottis 30, compression thereof causing the epiglottis 22 to raise up to expose the larynx 28 of the patient for viewing by the person performing the laryngoscopy. It can be appreciated that while the blade member 44 is being inserted into the vallecula epiglottica 30, the medical professional performing the laryngoscopy can view the area adjacent the tip of the blade member 44 through the eyepiece 66 and thus, ensure proper placement of the blade member 44 in the mouth 18 of the patient. By being able to view the area proximate to the tip of the blade member 44, the medical professional can ensure that the blade member 44 does not cause trauma or damage to the throat of the patient.

As is further illustrated in FIG. 1, the blade member described, provides two sources of light down the throat of the patient. The lamp member 64 provides light from the proximal end of the laryngoscope and, to a degree, illuminates the mouth and the pharynx of the patient. The light transmitted by fiber optic bundle 60 illuminates the area proximate to the distal end of the blade member 44.

While a preferred embodiment has been shown, modifications and changes may become apparent to those skilled in the art which shall fall within the spirit and scope of the invention. It is intended that such modifications and changes be covered by the attached claims.

I claim:

1. A laryngoscope which comprises a handle member adapted to receive batteries therein, a blade member having distal and proximal ends, means for attaching the proximal end of the blade member to the handle member, said blade member having a spatula portion curved longitudinally along its length and transversely across its width to provide an open bottom U-shaped tubulation and viewing channel along its length when inserted in the mouth of the user, a lamp member energized by batteries in the handle suspended from the proximal end of the blade member, below and facing said tubulation and viewing channel to illuminate for viewing and tubulation channel in the area between the distal and proximal ends of the spatula portion of said blade member, a first fiber optic bundle extending lengthwise on one leg of the tubulation an viewing channel from adjacent said lamp member and transmitting short of the distal end of the spatula to receive light from the lamp member and illuminate the area adjacent the distal end of the blade member, a lens on the proximal end of the blade member, a second fiber optic bundle extending lengthwise on the opposite leg of the channel terminating adjacent the distal end of the blade member beyond said first bundle to transmit the lighted view from adjacent said distal end to said lens, and said tubulation and viewing channel portion between the fiber optic bundles being unimpeded for tubulation and providing a clear sight path from the proximal end of the blade member along length of the spatula portion.

2. The laryngoscope of claim 1 including a wide dispersion lens on the distal end of the first fiber optic bundle to widely disperse the light emitted therefrom.

3. The laryngoscope of claim 1 including a second lens coupled to the distal end of the second fiber optic bundle to focus the light to the proximal end of the blade.

4. A laryngoscope blade member having proximal and distal ends with means at the proximal end for attachment to a battery carrying handle, a longitudinally elongated spatula portion between said ends, said spatula portion being transversely curved along its length to provide a viewing and tubulation channel which is open along its length, a lamp means suspended from the proximal end of the blade adapted to be energized from batteries in a handle attached to the blade and positioned to illuminate the tubulation channel in the area between the distal and proximal ends of the blade, a fiber optic bundle extending along one side of the channel for transmitting light from the lamp means to the area surrounding the distal end of the blade, and said lamp means and said bundle being positioned out of the viewing and tubulation portion of the channel to provide an unobstructed viewing and tubulation path along the length of the spatula portion.

5. The blade member of claim 4 including an upstanding leg means at the proximal end thereof mounting said lamp means below the viewing channel.

6. The laryngoscope of claim 4 including a second fiber optic bundle transmitting the view from the illuminated distal area of the spatula portion to the proximal end of the blade.

7. A laryngoscope blade having a proximal and distal ends and adapted to be affixed to a battery carrying laryngoscope handle member at its proximal end, said blade having a spatula portion between the proximal and distal ends of the blade, said spatula portion being curved longitudinally about its midpoint to embrace the tongue and throat of a user and also being curved transversely along its length to provide an open bottom viewing and tubulation channel with opposite sides, a lamp means attached to the proximal end of the blade adapted to be energized from batteries in the handle to illuminate the viewing and tubulation channel in the area between the distal and proximal end of the blade, a first fiber optic bundle along the length of the spatula portion at one side of the channel adapted to transmit light from the lamp means toward the distal end of the blade, a second fiber optic bundle attached along the length of the opposite side of the channel adapted to transmit the view from the light illuminated distal end portion of the blade to the proximal end of the blade, a viewing lens at the proximal end of the blade attached to said second optic bundle, and said first and second fiber optic bundles being positioned out of the path of said viewing and tubulation channel.

* * * * *